US011833308B2

(12) United States Patent
Koch

(10) Patent No.: US 11,833,308 B2
(45) Date of Patent: *Dec. 5, 2023

(54) SENSOR ADAPTOR, APPARATUS, AND METHOD FOR MONITORING END-TIDAL CARBON DIOXIDE

(71) Applicant: Carol Koch, Riverview, MI (US)

(72) Inventor: Carol Koch, Riverview, MI (US)

(73) Assignee: Carol Koch, Riverview, MI (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/117,362

(22) Filed: Dec. 10, 2020

(65) Prior Publication Data

US 2021/0085909 A1     Mar. 25, 2021

Related U.S. Application Data

(60) Division of application No. 15/907,720, filed on Feb. 28, 2018, now Pat. No. 10,881,828, which is a (Continued)

(51) Int. Cl.
*A61M 16/08*     (2006.01)
*A61M 16/00*     (2006.01)
(Continued)

(52) U.S. Cl.
CPC ........... *A61M 16/085* (2014.02); *A61B 5/082* (2013.01); *A61B 5/0836* (2013.01); *A61B 5/097* (2013.01);
(Continued)

(58) Field of Classification Search
CPC ................ A61M 16/06; A61M 16/085; A61M 2202/0225; A61M 2230/432; A61B 5/0836; A61B 5/085; A61B 5/097; A61B 5/6803
See application file for complete search history.

(56) References Cited

U.S. PATENT DOCUMENTS 5,311,862 A     5/1994 Blasdell et al.
5,400,781 A *   3/1995 Davenport .......... A61M 16/085
                                                  128/206.28

(Continued)

FOREIGN PATENT DOCUMENTS

WO     2013021172     2/2013
WO     WO-2013021172 A1 *  2/2013 ........... A61B 5/0836

OTHER PUBLICATIONS

Website: http://southmedic.com/products/oxymask-etco2/, OxyMaskTM ETCO2, pp. 1-2.

(Continued)

*Primary Examiner* — Joseph D. Boecker
(74) *Attorney, Agent, or Firm* — Dickinson Wright PLLC

(57) ABSTRACT

A sensor adaptor couples a face mask to a gas sampling tube connected to a device detecting end-tidal carbon dioxide. The sensor adaptor includes a shaft and connector. The shaft includes a channel providing a pathway for the carbon dioxide to travel toward the gas sampling tube. One end of the shaft includes an adaptor tip which extends through an exit port of the face mask. A connector is attached to the other end of the shaft and couples the sensor adaptor to the gas sampling line. A gripper may surround the shaft and prevent improper advancement of the shaft into the face mask. The sensor adaptor can be designed for use with any gas sampling tube and any face mask including exit ports.

7 Claims, 4 Drawing Sheets

Related U.S. Application Data continuation-in-part of application No. 14/159,932, filed on Jan. 21, 2014, now abandoned.

(60) Provisional application No. 61/768,620, filed on Feb. 25, 2013.

(51) Int. Cl.

| | |
|---|---|
| *A61M 16/06* | (2006.01) |
| *A61B 5/097* | (2006.01) |
| *A61B 5/083* | (2006.01) |
| *A61B 5/08* | (2006.01) |
| *A61B 5/00* | (2006.01) |

(52) U.S. Cl.
CPC ....... *A61B 5/6803* (2013.01); *A61M 16/0003* (2014.02); *A61M 16/06* (2013.01); *A61M 2202/0208* (2013.01); *A61M 2202/0225* (2013.01); *A61M 2205/3327* (2013.01); *A61M 2230/432* (2013.01)

(56) References Cited

U.S. PATENT DOCUMENTS

| | | | | |
|---|---|---|---|---|
| 5,431,158 | A | | 7/1995 | Tirotta |
| 5,474,060 | A | * | 12/1995 | Evans ............ A61B 5/097 |
| | | | | 128/204.22 |
| 7,004,163 | B2 | | 2/2006 | Nashed |
| 7,500,482 | B2 | | 3/2009 | Biederman |
| 7,614,401 | B2 | | 10/2009 | Thompson |
| 8,336,549 | B2 | | 12/2012 | Nashed |
| 8,365,734 | B1 | | 2/2013 | Lehman |
| 10,881,828 | B2 | * | 1/2021 | Koch ............ A61M 16/0003 |
| 2003/0047188 | A1 | | 3/2003 | Mace et al. |
| 2004/0060443 | A1 | | 4/2004 | Richardson |
| 2012/0271187 | A1 | * | 10/2012 | McNeill ............ A61B 5/097 |
| | | | | 600/532 |
| 2014/0243698 | A1 | * | 8/2014 | Koch ............ A61B 5/6803 |
| | | | | 29/428 |
| 2016/0038709 | A1 | * | 2/2016 | Beard ............ A61B 5/097 |
| | | | | 128/205.12 |

OTHER PUBLICATIONS

Mercury Medical, Capnography Masks, OxyMask, p. 99.
Website: http://flexicare.com/en/products/oxygen-aerosol-therapy/variable-concentration/cap . . . , Capnography and Co2 Monitoring, pp. 1-2.
Intersurgical Complete Respiratory Systems, The Sentri Range of End Tidal CO2 Monitoring Products, informational sheet/oxygen therapy, p. 1.
Mercury Medical, Capnography/Oxygen Masks, p. 100.
Website: http://monitormask.com/about-m1/, M! simplifies EtCO2 sedation monitoring for Anesthesia patients/Monitor Mask, p. 1-2.
Website: https://www.drivemedial.com/index.php/oxygen-mask-320.html, Oxygen Mask, p. 1.
Website: http://www.boundtree.com/filterline-nasal-inv-line-178174-pharm-5584-121.aspx, FilterLine Nasal/NIV Line, Adult, Kendall Healthcare Products, Co., p. 1.
Website: https://www.boundtree.com/smart-capnoline-co2-sampling-line-177268-pharm-5567-121 . . . , Smart CapnoLine CO2 Sampline Line, With O2 Tubing, Disposable, Adult/Intermediate, Kendall Healthcare Products Co., p. 1.
Clinical Standards Respironics, Standards for Capnography, American Society of Anesthesiologists (ASA)—Standard for Basic Anesthetic Monitoring 2010 Update, Nov. 2012, pp. 1-2.
Standards for Basic Anesthetic Monitoring, Committee of Origin: Standards and Practice Parameters, Approved by the ASA House of Delegates on Oct. 21, 1986, and last amended on Oct. 20, 2010 with an effective date of Jul. 1, 2011, p. 1.

* cited by examiner

SENSOR ADAPTOR, APPARATUS, AND METHOD FOR MONITORING END-TIDAL CARBON DIOXIDE

CROSS REFERENCE TO RELATED APPLICATION

This U.S. divisional patent application claims the benefit of U.S. utility patent application Ser. No. 15/907,720, filed Feb. 28, 2018, which is a Continuation-In-Part of U.S. non-provisional application Ser. No. 14/159,932, filed Jan. 21, 2014 and claims the benefit of U.S. provisional patent application No. 61/768,620, filed Feb. 25, 2013, the content of which are incorporated herein by reference in its entirety.

BACKGROUND OF THE INVENTION

1. Field of the Invention

The invention relates generally to an apparatus for improving detection of the presence of a patient's end-tidal carbon dioxide, a method of forming the apparatus, and a method for improving detection of end-tidal carbon dioxide.

2. Related Art

In the field of health care, patients under the care of a practitioner oftentimes require oxygen delivery. Various different techniques can be used to deliver oxygen to the patient. One technique includes the use of a face mask, such as a simple face mask, with an opening in the nose region for receiving an oxygen delivery tube. When the face mask is used to deliver oxygen, the patient's exhaled carbon dioxide, referred to as end-tidal carbon dioxide ($CO_2$), must be monitored. The presence or absence of end-tidal carbon dioxide provides valuable information to the practitioner. For example, the absence of end-tidal carbon dioxide indicates there could be an obstruction in the patient's airway, which could threaten the patient's health or safety. Thus, it a reliable method of monitoring end-tidal carbon dioxide is necessary.

One technique currently used to detect end-tidal carbon dioxide includes the use of an anesthesia machine, for example a D-Fend™. The practitioner manually lifts the face mask slightly off the patient's face, and places a gas sampling tube connected to the machine underneath the face mask. However, when this technique is used, the practitioner must manually hold the gas sampling tube in place, or carefully watch the patient to make sure the gas sampling tube remains in the correct position. The gas sampling tube must not obstruct oxygen delivery or slip out from under the face mask. If the gas sampling tube is moved from the correct position, the anesthesia machine is unable to accurately detect the presence or absence of the patient's end-tidal carbon dioxide, and the patient's health and safety could be at risk. There is clearly a need for more convenient and reliable methods of detecting a patient's end-tidal carbon dioxide.

SUMMARY OF THE INVENTION

One aspect of the invention comprises a sensor adaptor which provides a secure, convenient, and reliable connection between a face mask and a gas sampling tube connected to a device detecting the presence or absence of the patient's end-tidal carbon dioxide. The sensor adaptor includes a shaft and a connector. The shaft has a generally tubular shape extending from a first end to a second end and including a shaft outer surface presenting a shaft outside diameter. The shaft outside diameter is not greater than an exit port diameter of the face mask for which the sensor adaptor is designed. The shaft also includes a shaft inner surface presenting a channel extending continuously from the first end to the second end for providing a continuous pathway from the underside of the face mask toward the gas sampling tube. The shaft also includes an adaptor tip adjacent the first end, which is disposed in the exit port of the face mask. The connector is attached to the shaft for coupling the channel of the shaft to the gas sampling tube.

In one embodiment, the sensor adaptor includes a gripper surrounding the shaft adjacent the first end and presenting the adaptor tip between the gripper and the first end of the shaft. The gripper includes a gripper outer surface presenting a gripper outside diameter which is greater than the shaft outside diameter.

Another aspect of the invention provides an apparatus for coupling to a device detecting the presence or absence of the patient's end-tidal carbon dioxide. The apparatus includes the face mask for disposing over the nose and mouth of a patient. The face mask includes a mask inner surface presenting an inner volume. The face mask also includes a nasal opening for receiving an oxygen delivery tube and a plurality of exit ports for allowing carbon dioxide to exit the inner volume. Each of the exit ports presents an exit port diameter. The apparatus also includes the sensor adaptor for coupling the face mask to a gas sampling tube connected to the device detecting the end-tidal carbon dioxide. The adaptor tip of the sensor adaptor is disposed in one of the exit ports of the face mask, and the shaft outside diameter is not greater than the exit port diameter of the one exit port in which the shaft is disposed.

Yet another aspect of the invention provides a method for manufacturing the apparatus for coupling to the device detecting the presence or absence of end-tidal carbon dioxide. The method includes providing the face mask, and disposing the sensor adaptor in one of the exit ports of the face mask. According to one embodiment, the step of disposing the sensor adaptor in one of the exit ports of the face mask includes inserting the adaptor tip into the exit port until the gripper engages the mask outer surface.

Another aspect of the invention provides a method for improving detection of the presence or absence of the patient's end-tidal carbon dioxide. The method includes providing the face mask and the sensor adaptor, and coupling the sensor adaptor to the face mask by inserting the adaptor tip through one of the exit ports of the face mask until the stopper end engages a mask outer surface. The method also includes coupling the oxygen delivery tube to the nasal opening of the face mask, and disposing the face mask over the nose and mouth of the patient. The method further includes coupling the connector end of the sensor adaptor to the gas sampling tube, which is connected to the device detecting the end-tidal carbon dioxide.

The sensor adaptor of the present invention provides numerous advantages. For example, the sensor adaptor can be used with any existing face mask including exit ports, such as the simple face mask. The adaptor tip and the exit port provide a tight frictional engagement or press fit therebetween. Thus, the sensor adaptor remains in the exit port of the face mask, even while patient moves about or moves the face mask, and provides a secure connection between the inner volume of the face mask, where the patient exhales carbon diode, and the gas sampling tube. In addition, the sensor adaptor does not obstruct oxygen delivery or prevent carbon dioxide from exiting the mask. If the practitioner needs to remove the sensor adaptor, he or she simply pulls the adaptor tip of the sensor adaptor out of the exit port. The reliability provided by the sensor adaptor allows for more rapid detection of an obstructed airway, or other potential safety issues, and thus improves the quality of care provided to the patient.

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE ENABLING EMBODIMENTS

Figure 1:
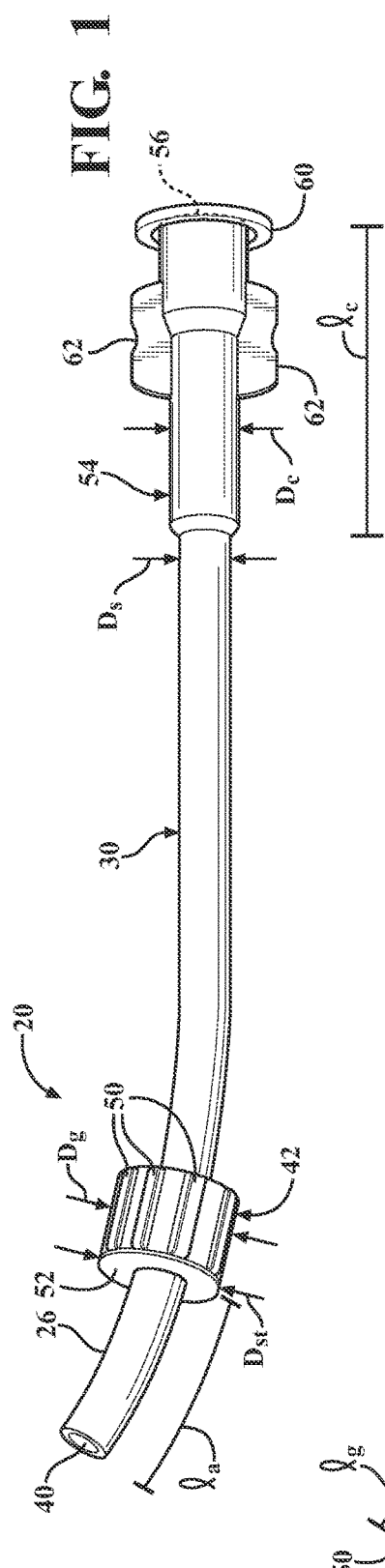
FIG. 1 is a perspective view of a sensor adaptor according to one exemplary embodiment of the invention.
Figure 2:
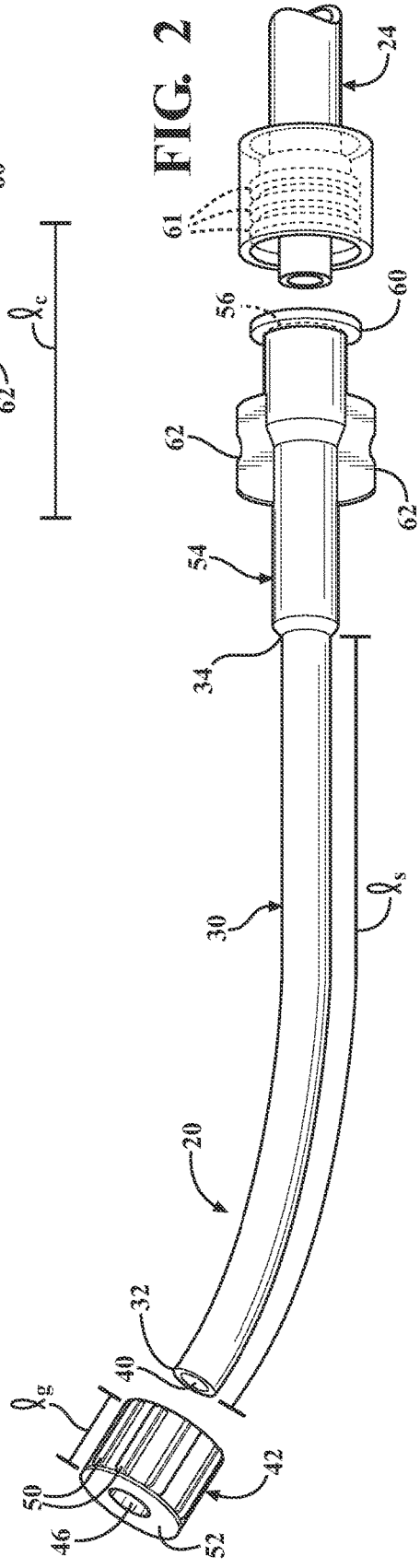
FIG. 2 is an exploded view of the sensor adaptor of FIG. 1 adjacent an end of an exemplary gas sampling tube.
Figure 3:
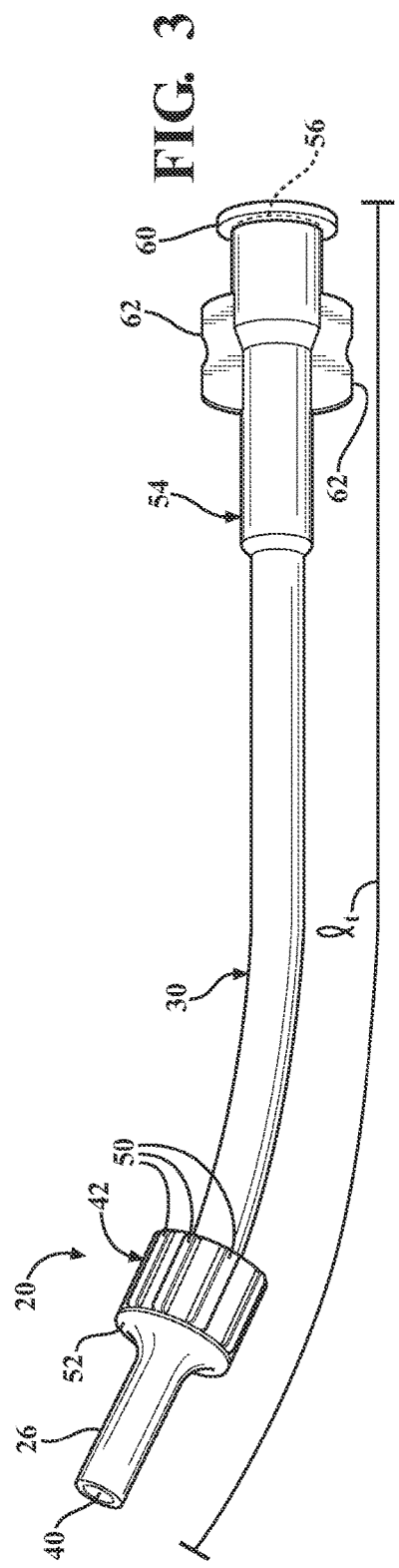
FIG. 3 is a perspective view of a sensor adaptor according to another exemplary embodiment of the invention.
Figure 4:
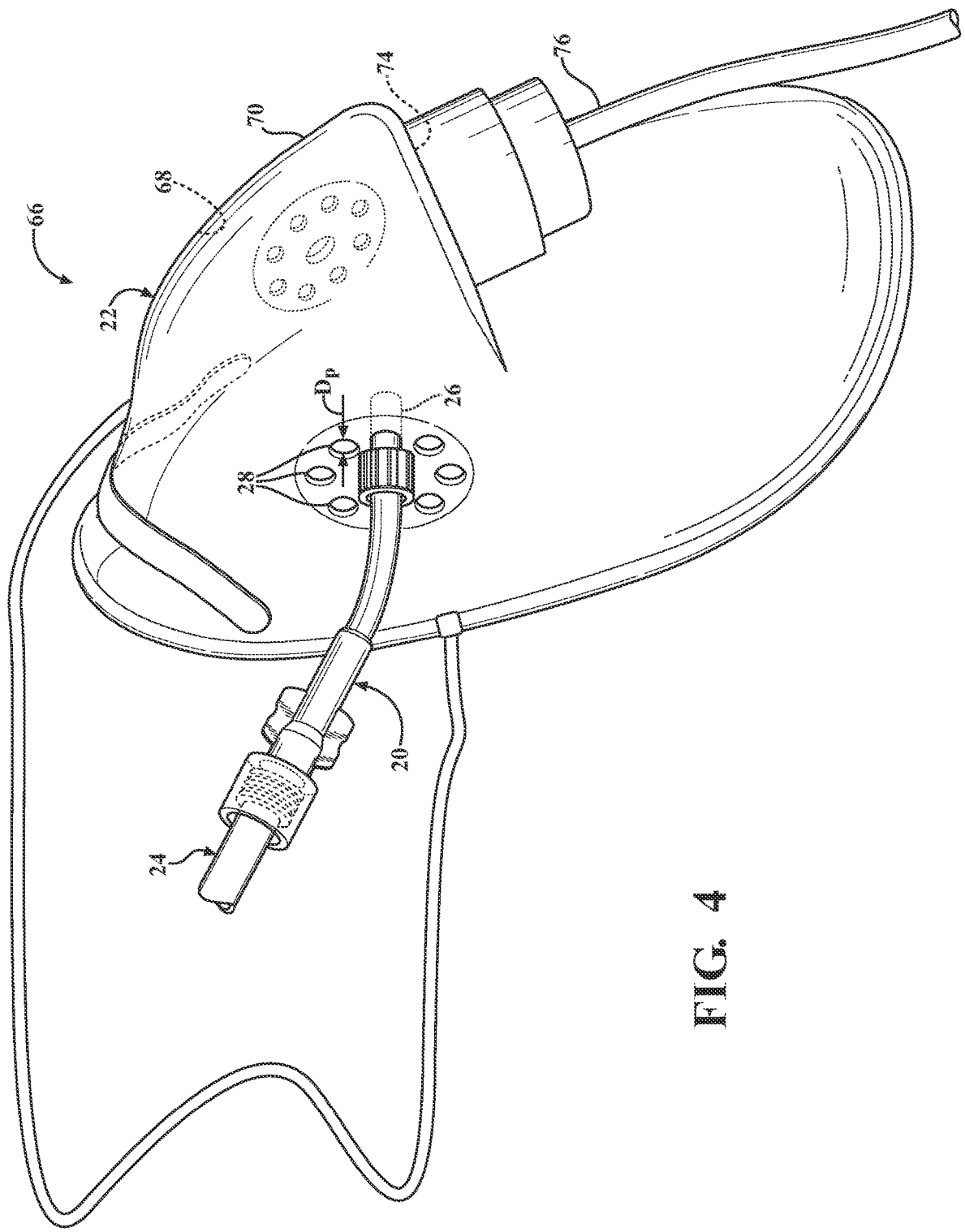
FIG. 4 is a perspective view of the sensor adaptor of FIGS. 1 and 2 connected to the gas sampling tube and inserted in an exit port of a face mask.

A sensor adaptor 20 for coupling a face mask 22 to a gas sampling tube 24, which is connected to a device detecting the presence and/or absence of a patient's end-tidal carbon dioxide, is generally shown in FIGS. 1-3. An adaptor tip 26 of the sensor adaptor 20 can be inserted through an exit port 28 of the face mask 22 to maintain a secure connection between the underside of the face mask 22 and the gas sampling tube 24, as shown in FIG. 4. The sensor adaptor 20 provides a quicker, more efficient, and more reliable method of detecting end-tidal carbon dioxide, compared to prior art methods of monitoring end-tidal $CO_2$, such as manually inserting an end of the standard gas sampling tube 24 underneath the face mask 22 and monitoring the patient to make sure the standard gas sampling tube 24 stays in position while the patient breathes.

The sensor adaptor 20 includes a shaft 30 having a generally tubular shape extending from a first end 32 to a second end 34 and a shaft length $l_s$ extending from the first end 32 to the second end 34. The shaft 30 includes a shaft outer surface which typically presents a cylindrical shape and has a shaft outside diameter $D_s$. The shaft outside diameter $D_s$ is designed so that it is not greater than an exit port diameter $D_p$ of one of the exit ports 28 of the face mask 22, through which the sensor adaptor 20 is inserted. This can be any one of many exit ports 28 including a plurality of circular holes arranged in a regular, circular pattern in a face mask 22. Typically, the shaft outside diameter $D_s$ is just slightly less than the exit port diameter $D_p$, so that the practitioner needs to exert a small amount of force to insert or remove the shaft 30 from the exit port 28. In one exemplary embodiment, the shaft outside diameter $D_s$ is approximately 0.1 to 0.5 cm, for example 0.3 cm. The shaft 30 also includes a shaft inner surface facing opposite the shaft outer surface. The shaft inner surface presents a channel 40 also typically having a cylindrical shape. The channel 40 is unobstructed and extends continuously from the first end 32 to the second end 34 of the shaft 30 to provide a direct pathway toward the gas sampling tube 24. The size and geometry of the channel 40 can vary for any reason, for example to provide the most efficient detection method.

The shaft 30 also includes an adaptor tip 26 adjacent the first end 32, which is inserted through the exit port 28 of the face mask 22. The adaptor tip 26 also presents the channel 40 providing the pathway toward the gas sampling tube 24. The adaptor tip 26 presents an adaptor length $l_a$ being a portion of the shaft length $l_s$. In the exemplary embodiment, the adaptor length $l_a$ is 0.3 cm to 1.0 cm, for example 0.5 cm. However, the adaptor length $l_a$ can vary. For example, the adaptor length $l_a$ can vary depending on the geometry and thickness of the face mask 22, or for other reasons.

Figure 5:
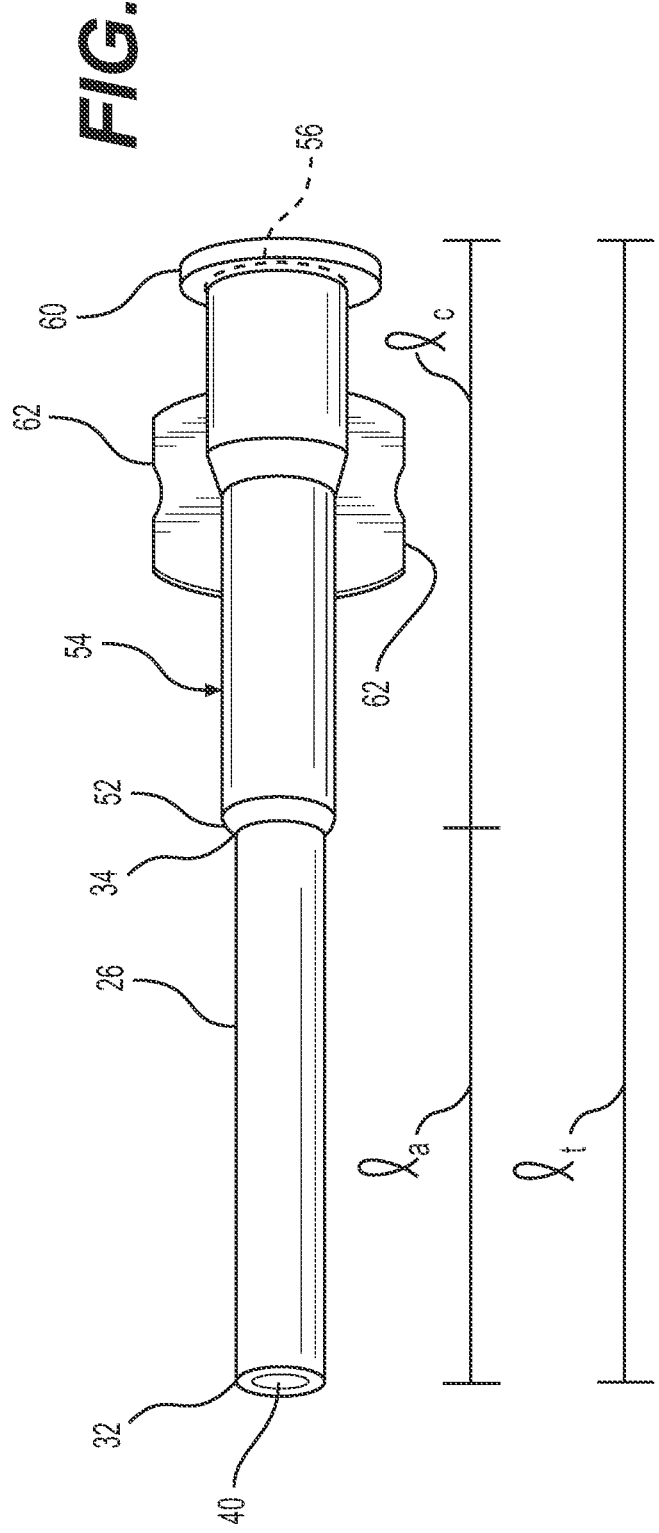
FIG. 5 is a perspective view of a sensor adaptor according to another exemplary embodiment of the invention.

The sensor adaptor 20 also typically includes a gripper 42 surrounding the shaft 30 adjacent the first end 32. However, the sensor adaptor 20 can be formed without the gripper 42. When present, the gripper 42 can comprise any shape. In the exemplary embodiment, the gripper 42 includes a gripper inner surface presenting a gripper opening 46 surrounding the shaft 30. The gripper 42 also includes a gripper outer surface presenting a gripper outside diameter $D_g$ which is greater than the shaft outside diameter $D_s$. The gripper 42 presents a gripper length $l_g$ extending along a portion of the shaft length $l_s$. In the exemplary embodiment, the gripper length $l_g$ is 0.5 cm to 1.5 cm, for example 1.0 cm. The gripper outer surface presents a plurality of grooves 50 extending parallel to the shaft 30 for allowing a practitioner to grip the sensor adaptor 20. The design of the grooves 50 can vary as desired. The gripper 42 allows the practitioner to easily control and position the sensor adaptor 20 relative to the face mask 22. In the embodiment of FIGS. 1, 2 and 4, the gripper 42 is manufactured separate from the shaft 30, and the first end 32 of the shaft 30 is inserted through the gripper opening 46 to form the sensor adaptor 20. In this embodiment, the gripper 42 and the shaft 30 present a tight frictional engagement or press fit therebetween. In the embodiment of FIG. 3, the gripper 42 and the shaft 30 are formed integral with one another, for example by a single molding process. As shown in the embodiment of FIG. 5, the sensor adaptor 20 may be provided without a gripper 42.

The gripper 42 may be fixed to the shaft 30 with the adaptor length $l_a$ being constant. For example, the gripper 42 may be integrally formed with the 30 or secured thereabout with an adhesive or a weld, or the like. Alternatively, the gripper 42 may be movable on the shaft 30 for allowing adjustment of the adaptor length $l_a$, for example, to allow for specific fitment to an individual patient.

The gripper 42 of the sensor adaptor 20 also includes a stopper end 52 comprising a surface facing generally toward the first end 32 of the shaft 30 for preventing improper advancement of the sensor adaptor 20 into the face mask 22. The stopper end 52 and the first end 32 of the shaft 30 present the adaptor tip 26 therebetween. The surface of the stopper end 52 can be planar and perpendicular to the shaft 30, as shown in FIGS. 1, 2, and 4, or disposed at another angle relative to the shaft 30, or slightly curved, as shown in FIG. 3. The surface of the stopper end 52 has a stopper diameter $D_{st}$ which is greater than the shaft outside diameter $D_s$. In the embodiments of FIGS. 1-4, the gripper 42 and the stopper end 52 are formed as a single component. However, the gripper 42 and the stopper end 52 could comprise separate components.

The sensor adaptor 20 also includes a connector 54 attached to the second end 34 of the shaft 30 for coupling the shaft 30 to the gas sampling tube 24. The connector 54 is typically separate from the gas sampling tube 24, but it could be formed integral with the gas sampling tube 24. Various different types of connectors 54 can be used. In the exemplary embodiment, the connector 54 includes a female Luer lock and the gas sampling tube 24 includes a male Luer, as shown in FIGS. 2 and 4. In this embodiment, the connector 54 of the adaptor presents a connector opening 56 which is in fluid communication with the channel 40 of the shaft 30. The connector 54 also has a connector end opposite the shaft 30 which is open so that an end of the gas sampling tube 24 can be received in the connector opening 56. At least one thread 60 extends radially outwardly from the connector 54 for engaging threads 61 of the male Luer lock at the end of the gas sampling tube 24. The connector 54 of the exemplary embodiment also includes a pair of wings 62 extending longitudinally along and radially outwardly, which can be gripped by the practitioner while attaching the female Luer lock to the male Luer lock. However, the connector 54 can alternatively be formed without the wings 62. The connector 54 also includes a connector outer surface presenting a connector outside diameter $D_c$ which is greater than the shaft outside diameter $D_s$. In the exemplary embodiment, the connector 54 presents a connector length $l_c$ of 2.0 cm to 2.8 cm, for example 2.4 cm, and the distance between the connector 54 and the gripper 42 is 1.5 cm to 2.5 cm, for example 2.0 cm. However, the connector length $l_c$ can vary for any reason.

The sensor adaptor 20 presents a total length $l_t$ extending from the open connector end to the first end 32 of the shaft 30. In the exemplary embodiment shown in FIG. 2, the total length $l_t$ of the sensor adaptor 20 is 5.0 cm to 6.5 cm, for example 5.9 cm. However, the total length $l_t$ of the sensor adaptor 20 can vary. The components of the sensor adaptor 20 are preferably each formed of a translucent or transparent plastic material, for example, clear material, but they could be formed of other materials having various different colors. As discussed above, the components of the sensor adaptor 20 are preferably formed integral with one another, such that the sensor adaptor 20 comprises a single piece. The components of the sensor adaptor 20 could alternatively be formed separate from one another, and then connected together. The shaft 30 is preferably formed of a pliable plastic material such as, for example, DEHP-Free PVC. This helps to prevent injury in case of contact with the patient, for example when inserting the adaptor tip 26 into the face mask 22. The connector 54 is preferably formed of a rigid plastic material such as, for example, Nylon polypropylene, polyethylene, or Kynar.

Another aspect of the invention provides an apparatus 66 for coupling to the device which detects at least one of the presence and absence of end-tidal carbon dioxide. The apparatus 66 includes the face mask 22 which is disposed over the nose and mouth of the patient. Various different types of face masks 22 can be used. However, in the exemplary embodiment shown in FIG. 4, the face mask 22 is a simple face mask. The face mask 22 can be formed of various different materials, but is preferably formed of a translucent or transparent plastic material. The face mask 22 includes a mask inner surface 68 which faces the nose and mouth of the patient and a mask outer surface 70 facing opposite the mask inner surface 68. As shown in FIG. 4, the mask inner surface 68 has a contour resembling the contour of the nose and mouth of the patient. The mask inner surface 68 also presents an inner volume between the mask inner surface 68 and the nose and mouth of the patient. When the patient exhales carbon dioxide, the carbon dioxide enters this inner volume.

The face mask 22 also includes a nose portion with a nasal opening 74 for receiving an oxygen delivery tube 76, as shown in FIG. 4, which delivers oxygen to the patient. The oxygen delivery tube 76 presents an airway being open for allowing oxygen to enter the inner volume of the face mask 22 and become accessible to the nose and mouth of the patient. The face mask 22 also includes a pair of generally flat side portions disposed on opposite sides of the nose portion. Each of the side portions extends in a common, generally parasagittal plane with said face mask disposed over the nose and mouth of the patient. In other words, with the face mask 22 being installed on a patent in an upright position, the side portions extend generally vertically and parallel to the sagittal plane that divides the patient's body into left and right halves. The side portions may tilt slightly inwardly toward the top and/or toward the front of the facemask. Each of the side portions also defines a plurality of the exit ports 28, which are arranged in a regular, circular pattern for allowing the end-tidal carbon dioxide to exit the inner volume.

As discussed above, each of the exit ports 28 presents an exit port diameter $D_p$, and at least one of the exit ports 28 has an exit port diameter $D_p$ which is slightly greater than or equal to the shaft outside diameter $D_s$ of the sensor adaptor 20, so that the sensor adaptor 20 can be inserted in that exit port 28. Typically, the exit ports 28 all have the same exit port diameter $D_p$, and the shaft outside diameter $D_s$ is designed to be approximately equal to the exit port diameter $D_p$.

Also shown in FIG. 4, the sensor adaptor 20 extends into one of the exit ports 28 of the face mask 22 and thus couples the inner volume presented by the mask inner surface 68 to the gas sampling tube 24. Also in the embodiment of FIG. 4, the sensor adaptor 20 is formed separate from the face mask 22, and thus can be inserted, removed, and re-inserted into the face mask 22 by the practitioner, as many times as necessary. In this embodiment, the shaft 30 is inserted so that it frictionally engages the wall of the exit port 28 and thus remains in tight in the exit port 28 while the patient wears the face mask 22. The sensor adaptor 20 remains in the exit port 28, even while patient moves about, and thus provides a secure connection between the inner volume of the simple face mask 22, where the patient exhales carbon diode, and the gas sampling tube 24. If the practitioner needs to remove the sensor adaptor 20, he or she simply pulls the sensor adaptor 20 out of the exit port 28.

In another embodiment, the sensor adaptor 20 is formed integral with the face mask 22 and thus is permanently attached to the face mask 22 to provide an even more secure connection between the inner volume and the gas sampling tube 24. In yet another embodiment, the sensor adaptor 20 is formed integral with the gas sampling tube 24. However, forming the sensor adaptor 20 separate from the face mask 22 or gas sampling tube 24 provides an advantage because then the sensor adaptor 20 can be used with any existing face mask that includes exit ports, or any existing gas sampling tube. This saves a significant amount of resources, and money, as new face masks do not need to be purchased. The sensor adaptor 20 can also be used with various different devices capable of detecting the presence and/or absence of patient's end-tidal carbon dioxide. For example, the device can be an anesthesia machine, such as a machine referred to as D-Fend™, or a device used in the rescue squad.

Figure 6:
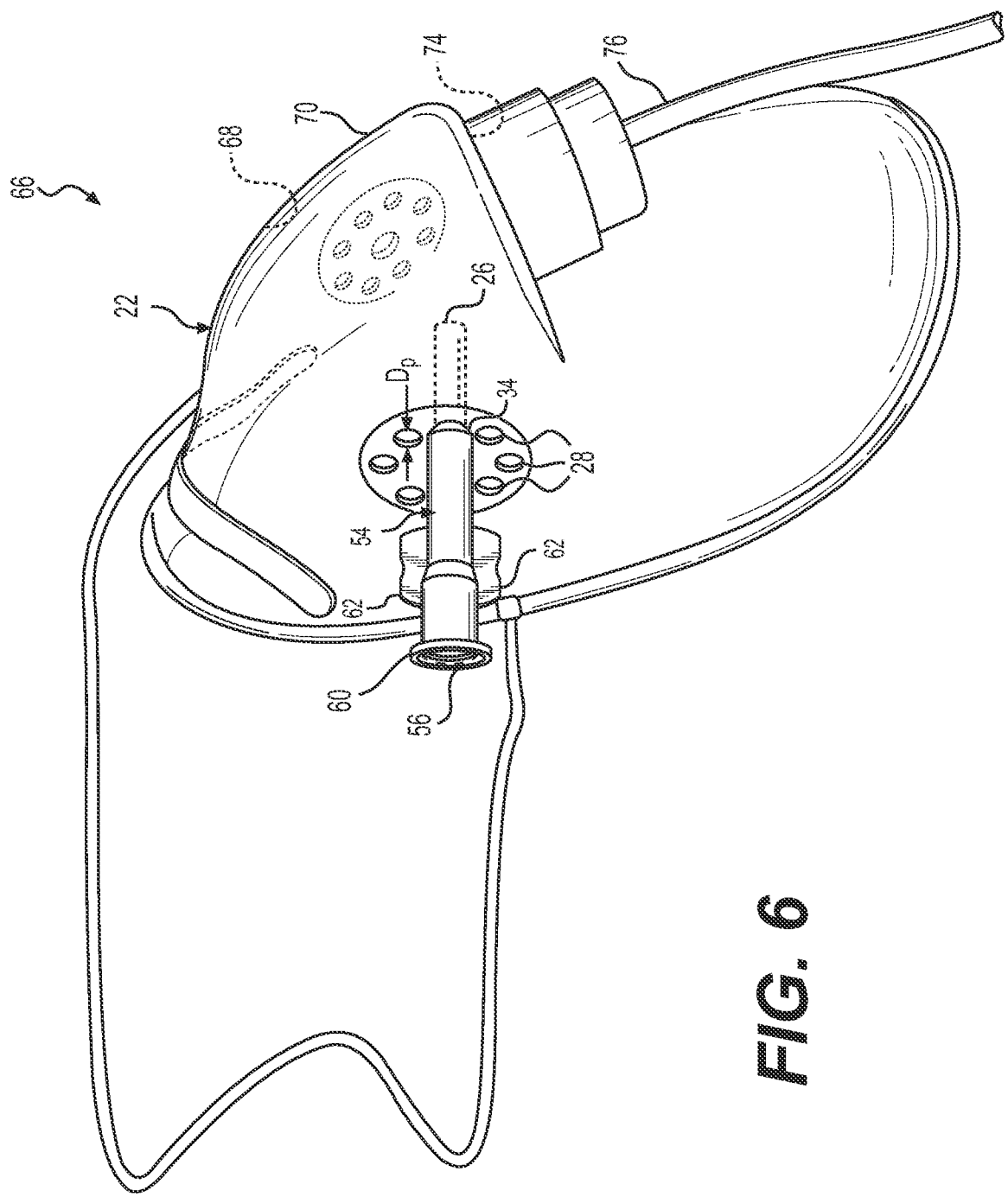
FIG. 6 is a perspective view of the sensor adaptor of FIG. 5 inserted in an exit port of a face mask.

FIG. 5 shows another embodiment of the sensor adaptor 20. In the embodiment of FIG. 5, the adaptor tip 26 extends the entire length of the shaft 30, and there is no gripper 42. In other words, the outer surface of the shaft 30 is exposed along its length between the first end 32 and the second end 32. The connector 54 defines the stopper end 52 extending radially outwardly from the shaft outer surface and facing the first end 32 for engaging the mask outer surface 70 to limit the insertion depth of the adaptor tip 26 within one of the circular holes of said exit port of the face mask 22. The adaptor tip 26 is preferably formed of a pliable plastic material having sufficient rigidity to resist kinking such as, for example, DEHP-Free PVC. This helps to prevent injury in case of contact with the patient, for example when inserting the adaptor tip 26 into the face mask 22. The adaptor length $l_a$ is preferably 0.3 cm to 1.5 cm, for example 0.5 cm. The connector length $l_c$ is preferably 2.0 cm to 2.8 cm. In the example embodiment shown, the adaptor length $l_a$ is 1.5 cm, and the connector length $l_c$ is 2.5 cm, providing the sensor adaptor 20 with a total length total length $l_t$ of 4.0 cm. The adaptor tip 26 has a shaft outside diameter $D_s$ that is preferably about the same as an exit port diameter $D_p$ of one of the exit ports 28 of the face mask 22, through which the sensor adaptor 20 is inserted. The shaft outside diameter $D_s$ is preferably about 0.3 cm. FIG. 6 illustrates the sensor adaptor 20 of FIG. 5 installed on a face mask 22.

Another aspect of the invention provides a method of manufacturing an apparatus 66 including the sensor adaptor 20 which is coupled to the device which detects the patient's end-tidal carbon dioxide. The method includes providing the face mask 22 including the plurality of exit ports 28, and disposing the sensor adaptor 20 in one of the exit ports 28 of the face mask 22. The step of disposing the sensor adaptor 20 in the exit port 28 of the face mask 22 preferably includes inserting the adaptor tip 26 into the exit port 28 until the gripper 42 engages the mask outer surface 70. At this point, the adaptor tip 26 is disposed in the inner volume of the face mask 22. The sensor adaptor 20 is designed so that the adaptor length $l_a$ is long enough to extend into the inner volume, but not so long that it touches the patient's face. When the sensor adaptor 20 is disposed in the exit port 28, the stopper end 52 prevents improper advancement of the shaft 30 into the inner volume of the face mask 22.

Another aspect of the invention provides a method for detecting the patient's end-tidal carbon dioxide. The method includes providing the face mask 22 and the sensor adaptor 20, as described above. The method next includes coupling the oxygen delivery tube 76 to the nasal opening 74 of the face mask 22, and disposing the face mask 22 over the nose and mouth of the patient to deliver oxygen to the patient. The method further includes coupling the connector end of the sensor adaptor 20 to the gas sampling tube 24 connected to the device monitoring the presence and/or absence of carbon dioxide in the inner volume of the simple face mask 22. The step of coupling the sensor adaptor 20 to the gas sampling tube 24 can be conducted either before or after the face mask 22 is disposed over the nose and mouth of the patient. When the sensor adaptor 20 is formed separate from the face mask 22, the step of coupling the sensor adaptor 20 to the face mask 22 includes inserting the adaptor tip 26 through one of the exit ports 28 of the face mask 22 until the stopper end 52 engages the mask outer surface 70. The sensor adaptor 20 remains securely connected to the face mask 22, and thus provides a convenient and reliable means to detect the presence or absence of end-tidal carbon dioxide in the inner volume of the face mask 22. The reliability provided by the sensor adaptor 20 allows for more rapid detection of airway obstruction, or other potential safety issues, and thus improves the quality of care provided to the patient.

Obviously, many modifications and variations of the present invention are possible in light of the above teachings and may be practiced otherwise than as specifically described while within the scope of the appended claims. In addition, although the term "diameter" is used to describe certain features of the invention, it is noted that those features do not necessary have a circular shape. Each of those features could comprise a rectangular shape, or another non-circular shape. Furthermore, although exemplary dimensions are disclosed for many components, it is noted that the components of the invention can comprise varies other dimensions.

What is claimed is:

1. A sensor adaptor for coupling a face mask to a gas sampling tube, comprising:
a shaft extending between a first end and a second end and defining a shaft length extending from said first end to said second end;
said shaft having a generally tubular shape including a shaft outer surface presenting a smooth cylindrical shape and a shaft inner surface opposite said shaft outer surface, and presenting a channel having a cylindrical shape, said channel being unobstructed and extending continuously from said first end to said second end for providing a direct pathway for end-tidal carbon dioxide to travel toward the gas sampling tube;
said shaft including an adaptor tip adjacent said first end for placement within the face mask and defining an adaptor length being a portion of said shaft length;
said shaft being exposed between said first end and said second end;
said sensor adaptor having no structure surrounding said shaft;
said adaptor length extending for the entirety of said shaft length;
a connector attached to said second end of said shaft for coupling said channel of said shaft to the gas sampling tube; and
said smooth cylindrical outer surface of said shaft outer surface extending substantially the entire length from said connector to said first end for providing a tight frictional press fit engagement within a circular hole of an exit port of the face mask.

2. The sensor adaptor of claim 1 wherein said shaft length is about 1.5 CM;
wherein said shaft is formed of a pliable plastic material; and
wherein said connector is formed of a rigid plastic material.

3. An apparatus for coupling to a gas sampling tube, comprising:
a face mask for disposing over a nose and mouth of a patient, said face mask including a generally flat side portion having a generally uniform thickness and defining an exit port including a circular hole therethrough;
wherein said generally flat side portion immediately surrounding said circular hole has said generally uniform thickness;
a sensor adaptor for coupling said face mask to the gas sampling tube and including a shaft extending from a first end to a second end, said shaft defining a shaft length extending from said first end to said second end, said shaft including a shaft outer surface presenting a smooth cylindrical shape with a shaft outside diameter providing a tight frictional press fit engagement within said circular hole of said exit port of said face mask, said shaft including a shaft inner surface presenting a channel extending continuously from said first end to said second end for providing a continuous pathway from said face mask toward the gas sampling tube, said shaft including an adaptor tip adjacent said first end for being disposed in the exit port of the face mask and defining an adaptor length being a portion of said shaft length, said shaft being exposed between said first end and said second end, and said sensor adaptor having no structure surrounding said shaft, and said adaptor length extending for the entirety of said shaft length;

a connector attached to said second end of said shaft for coupling said channel of said shaft to the gas sampling tube; and said smooth cylindrical outer surface of said shaft outer surface extending substantially the entire length from said connector to said first end for providing the tight frictional press fit engagement within said circular hole of said exit port of said face mask.

4. The apparatus of claim 3, wherein the gas sampling tube is connected to a device detecting at least one of the presence and absence of end-tidal carbon dioxide.

5. A method for manufacturing an apparatus, comprising:

providing a face mask including a mask outer surface and a mask inner surface presenting an inner volume, the face mask including a generally flat side portion extending in a generally common plane and defining a plurality of exit ports for allowing carbon dioxide to exit the inner volume, each of the exit ports presenting an exit port diameter;

disposing a sensor adaptor in one of the exit ports of the face mask in a tight frictional press fit engagement, the sensor adaptor including a shaft extending from a first end to a second end, the shaft including a shaft outer surface presenting a smooth cylindrical shape with a shaft outside diameter being approximately equal to the exit port diameter of the face mask for providing the tight frictional press fit engagement between said shaft outer surface and said exit port, the shaft including an inner surface presenting a channel extending continuously from the first end to the second end, and the shaft including an adaptor tip adjacent the first end, the sensor adaptor including a connector adjacent the second end, with said smooth cylindrical outer surface of said shaft outer surface extending substantially the entire length from the connector to the first end for providing the tight frictional press fit engagement within the exit port of the face mask; and wherein the step of disposing the sensor adaptor in one of the exit ports of the face mask in the tight frictional press fit engagement includes inserting the adaptor tip into the exit port until a stopper end extending radially outwardly beyond the shaft outer surface and facing the first end engages the mask outer surface.

6. The method of claim 5 wherein the connector defines the stopper end; and wherein the step of disposing the sensor adaptor in one of the exit ports of the face mask in the tight frictional press fit engagement includes inserting the adaptor tip into the exit port until the connector engages the mask outer surface.

7. The method of claim 5, wherein the apparatus is designed for coupling to a device detecting at least one of the presence and absence of end-tidal carbon dioxide.

\* \* \* \* \*